(12) United States Patent
Strasfeld et al.

(10) Patent No.: US 11,426,075 B1
(45) Date of Patent: Aug. 30, 2022

(54) SYSTEM AND METHOD FOR RESIDUAL CANCER CELL DETECTION

(71) Applicant: Lumicell, Inc., Wellesley, MA (US)

(72) Inventors: David B. Strasfeld, Cambridge, MA (US); W. David Lee, Brookline, MA (US); Jorge Ferrer, Arlington, MA (US)

(73) Assignee: Lumicell, Inc., Newton, MA (US)

( * ) Notice: Subject to any disclaimer, the term of this patent is extended or adjusted under 35 U.S.C. 154(b) by 713 days.

(21) Appl. No.: 15/684,627

(22) Filed: Aug. 23, 2017

(51) Int. Cl.
| | | |
|---|---|---|
| *A61B 5/00* | (2006.01) | |
| *G01N 33/483* | (2006.01) | |
| *A61K 49/00* | (2006.01) | |
| *G01N 21/64* | (2006.01) | |
| *A61B 90/00* | (2016.01) | |

(52) U.S. Cl.
CPC .......... *A61B 5/0071* (2013.01); *A61B 5/0082* (2013.01); *A61B 5/4848* (2013.01); *A61B 5/742* (2013.01); *A61K 49/0019* (2013.01); *G01N 21/6486* (2013.01); *G01N 33/4833* (2013.01); *A61B 90/37* (2016.02); *A61B 2090/373* (2016.02)

(58) Field of Classification Search
None
See application file for complete search history.

(56) References Cited

U.S. PATENT DOCUMENTS

| | | |
|---|---|---|
| 5,647,368 A | 7/1997 | Zeng et al. |
| 5,749,830 A | 5/1998 | Kaneko et al. |
| 6,069,689 A | 5/2000 | Zeng et al. |
| 6,537,211 B1 | 3/2003 | Wang et al. |
| 7,128,894 B1 | 10/2006 | Tannous et al. |
| 7,285,089 B2 | 10/2007 | Viellerobe et al. |
| 8,936,629 B2 | 1/2015 | Boyden et al. |
| 8,983,581 B2 | 3/2015 | Bawendi et al. |

(Continued)

FOREIGN PATENT DOCUMENTS

WO    WO 03/105814 A1    12/2003

OTHER PUBLICATIONS

Jiang et al., "Toward real-time quantification of fluorescence molecular probes using target/background ratio for guiding biopsy and endoscopic therapy of esophageal neoplasia", Journal of Medical Imaging, vol. 4, Issue 2, pp. 1-10, May 24, 2017. (Year: 2017).*

(Continued)

*Primary Examiner* — Katherine L Fernandez
(74) *Attorney, Agent, or Firm* — Wolf, Greenfield & Sacks, P.C.

(57) ABSTRACT

Embodiments related to methods of use of an image analysis system for identifying residual cancer cells after surgery are disclosed. In some embodiments, the image analysis system collects a surgical site image and indicates on a display one or more locations of the identified cancer cells. In some embodiments, the method for identifying residual cancer cells comprises determining and selecting a portion of the surgical site image responsive to an intensity parameter; modifying the selected portion of the surgical site image to determine one or more groups of residual cancer cells based on size; and identifying at least one of the one or more groups of residual cancer cells from the modified portion of the surgical site image using a local-based threshold.

14 Claims, 10 Drawing Sheets

(56) References Cited

U.S. PATENT DOCUMENTS

| | | | |
|---|---|---|---|
| 9,032,965 B2 | 5/2015 | Lee | |
| 9,155,471 B2 | 5/2015 | Lee | |
| 9,314,304 B2 | 4/2016 | Lee et al. | |
| 9,532,835 B2 | 1/2017 | Lee | |
| 9,738,937 B1* | 8/2017 | Hsieh | G01N 1/31 |
| 9,763,577 B2 | 9/2017 | Lee et al. | |
| 10,039,603 B2 | 8/2018 | Lee et al. | |
| 10,285,759 B2 | 5/2019 | Lee et al. | |
| 2003/0138378 A1 | 7/2003 | Hashimshony | |
| 2003/0190064 A1 | 10/2003 | Inoue et al. | |
| 2004/0147843 A1 | 7/2004 | Bambot et al. | |
| 2004/0186363 A1 | 9/2004 | Smit et al. | |
| 2005/0207668 A1 | 9/2005 | Perchant et al. | |
| 2006/0089554 A1 | 4/2006 | Ishihara et al. | |
| 2008/0015446 A1 | 1/2008 | Mahmood et al. | |
| 2008/0029711 A1 | 2/2008 | Viellerobe et al. | |
| 2008/0058795 A1 | 3/2008 | Boyden et al. | |
| 2008/0116392 A1 | 5/2008 | Brooker | |
| 2009/0202119 A1 | 8/2009 | Hefti et al. | |
| 2009/0220430 A1 | 9/2009 | Rajopadhye et al. | |
| 2009/0299196 A1 | 12/2009 | Bawendi et al. | |
| 2010/0158332 A1* | 6/2010 | Rico | A61B 5/4312 382/128 |
| 2010/0260422 A1 | 10/2010 | Ito et al. | |
| 2010/0262017 A1 | 10/2010 | Frangioni et al. | |
| 2011/0021908 A1 | 1/2011 | Lee et al. | |
| 2011/0042580 A1 | 2/2011 | Wilson et al. | |
| 2011/0104071 A1 | 5/2011 | Lee et al. | |
| 2012/0129165 A1* | 5/2012 | Raj | C12Q 1/6827 435/6.11 |
| 2012/0150164 A1 | 6/2012 | Lee et al. | |
| 2014/0088384 A1 | 3/2014 | Basillion | |
| 2014/0276102 A1* | 9/2014 | Lee | A61B 5/0086 600/476 |
| 2014/0276103 A1 | 9/2014 | Lee et al. | |
| 2014/0301950 A1 | 10/2014 | Lee et al. | |
| 2015/0314019 A1* | 11/2015 | Sokolov | A61K 49/0093 424/9.6 |

OTHER PUBLICATIONS

U.S. Appl. No. 14/847,434, filed Sep. 8, 2015, W. David Lee et al.
U.S. Appl. No. 15/203,104, filed Jul. 6, 2016, W. David Lee et al.
U.S. Appl. No. 15/721,247, filed Sep. 29, 2017, W. David Lee et al.
U.S. Appl. No. 14/211,201, filed Mar. 14, 2014, W. David Lee et al.
U.S. Appl. No. 15/206,754, filed Jul. 11, 2016, W. David Lee et al.
U.S. Appl. No. 14/211,259, filed Mar. 14, 2014, W. David Lee et al.
Pasternack et al., Highly sensitive size discrimination of sub-micron objects using optical Fourier processing based on two-dimensional Gabor filters. Opt Express. Jul. 6, 2009;17(14):12001-12.
[No Author Listed], Cathepsin Activatable Fluorescent Probe. Clinical Trials. Jun. 21, 2012. (https://clinicaltrials.gov/archive/NCT01626066/2012_06_21) [last accessed May 27, 2015].
Anikijenko et al., In vivo detection of small subsurface melanomas in athymic mice using noninvasive fiber optic confocal imaging. J Invest Dermatol. Dec. 2001;117(6):1442-8.
Bach et al., Elevated lysosomal pH in Mucolipidosis type IV cells. Clin Chim Acta. Feb. 1999;280(1-2):173-9.
Bates et al., Short-range spectroscopic ruler based on a single-molecule optical switch. Phys Rev Lett. Mar. 18, 2005;94(10):108101. Epub Mar. 15, 2005.
Bigio et al., Diagnosis of breast cancer using elastic-scattering spectroscopy: preliminary clinical results. J Biomed Opt. Apr. 2000;5(2):221-8.

Blum et al., Noninvasive optical imaging of cysteine protease activity using fluorescently quenched activity-based probes. Nat Chem Biol. Oct. 2007;3(10):668-77. Epub Sep. 9, 2007.
Brigman, Preliminary Analysis of Phase 1, First-In-Human, Cathepsin Activated Tumor Imaging Probe. Presentation. Nov. 2013. 29 pages.
Cheng et al., Near-infrared fluorescent RGD peptides for optical imaging of integrin alphavbeta3 expression in living mice. Bioconjug Chem. Nov.-Dec. 2005;16(6):1433-41.
Cuneo et al., Imaging primary mouse sarcomas after radiation therapy using cathepsin-activatable fluorescent imaging agents. Int J Radiat Oncol Biol Phys. May 1, 2013;86(1):136-42. doi: 10.1016/j.ijrobp.2012.12.007. Epub Feb. 4, 2013.
Dacosta et al., New optical technologies for earlier endoscopic diagnosis of premalignant gastrointestinal lesions. J Gastroenterol Hepatol. Feb. 2002;17 Suppl:S85-104.
De Grand et al., Tissue-like phantoms for near-infrared fluorescence imaging system assessment and the training of surgeons. J Biomed Opt. Jan.-Feb. 2006;11(1):014007.
Demos et al., Near-infrared autofluorescence imaging for detection of cancer. J Biomed Opt. May-Jun. 2004;9(3):587-92.
Funovics et al., Protease sensors for bioimaging. Anal Bioanal Chem. Nov. 2003;377(6):956-63. Epub Sep. 3, 2003.
Gleysteen et al., Fluorescent labeled anti-EGFR antibody for identification of regional and distant metastasis in a preclinical xenograft model. Head Neck. Jun. 2008;30(6):782-9. doi: 10.1002/hed.20782.
Graves et al., A submillimeter resolution fluorescence molecular imaging system for small animal imaging. Med Phys. May 2003;30(5):901-11.
Gray et al., Dual-mode laparoscopic fluorescence image-guided surgery using a single camera. Biomed Opt Express. Aug. 1, 2012;3(8):1880-90. doi: 10.1364/BOE.3.001880. Epub Jul. 17, 2012.
Hart et al., Cell binding and internalization by filamentous phage displaying a cyclic Arg-Gly-Asp-containing peptide. J Biol Chem. Apr. 29, 1994;269(17):12468-74.
Hingtgen et al., Real-time multi-modality imaging of glioblastoma tumor resection and recurrence. J Neurooncol. Jan. 2013;111(2):153-61. doi: 10.1007/s11060-012-1008-z. Epub Dec. 16, 2012.
Hsiung et al., Detection of colonic dysplasia in vivo using a targeted heptapeptide and confocal microendoscopy. Nat Med. Apr. 2008;14(4):454-8. doi: 10.1038/nm1692. Epub Mar. 16, 2008.
Liu et al., Hands-free, wireless goggles for near-infrared fluorescence and real-time image-guided surgery. Surgery. May 2011;149(5):689-98. doi: 10.1016/j.surg.2011.02.007.
Mahmood et al., Near-infrared optical imaging of protease activity for tumor detection. Radiology. Dec. 1999;213(3):866-70.
Ramanujam et al., Fast and noninvasive fluorescence imaging of biological tissues in vivo using a flying-spot scanner. IEEE Trans Biomed Eng. Sep. 2001;48(9):1034-41.
Reinisch, Laser physics and tissue interactions. Otolaryngol Clin North Am. Dec. 1996;29(6):893-914.
Singletary et al., Revision of the American Joint Committee on Cancer staging system for breast cancer. J Clin Oncol. Sep. 1, 2002;20(17):3628-36.
Tung et al., In vivo imaging of proteolytic enzyme activity using a novel molecular reporter. Cancer Res. Sep. 1, 2000;60(17):4953-8.
Weissleder et al., In vivo imaging of tumors with protease-activated near-infrared fluorescent probes. Nat Biotechnol. Apr. 1999;17(4):375-8.
Weissleder et al., In vivo magnetic resonance imaging of transgene expression. Nat Med. Mar. 2000;6(3):351-4.
Yang et al., Presentation, 2010 IVIS Imaging System from Caliper LifeSciences, 104 slide presentation 52 pages.
Zaheer et al., In vivo near-infrared fluorescence imaging of osteoblastic activity. Nat Biotechnol. Dec. 2001;19(12):1148-54.
Zornig et al., Re-excision of soft tissue sarcoma after inadequate initial operation. Br J Surg. Feb. 1995;82(2):278-9.

* cited by examiner

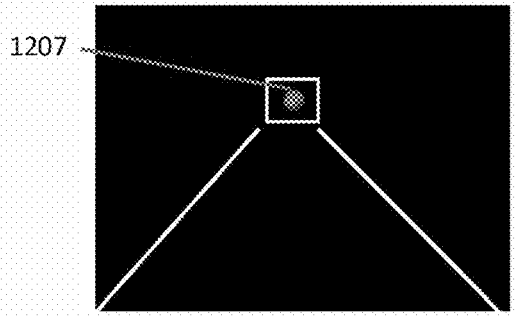 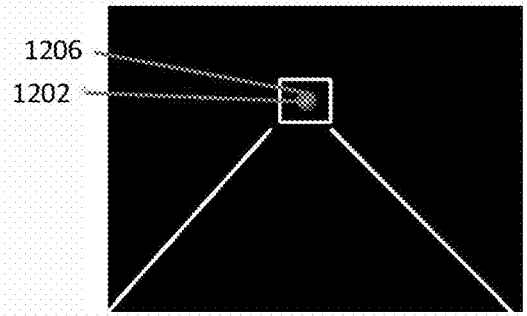
FIG. 12A    FIG. 12B
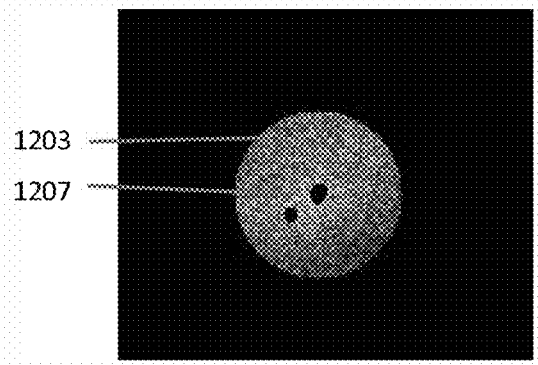 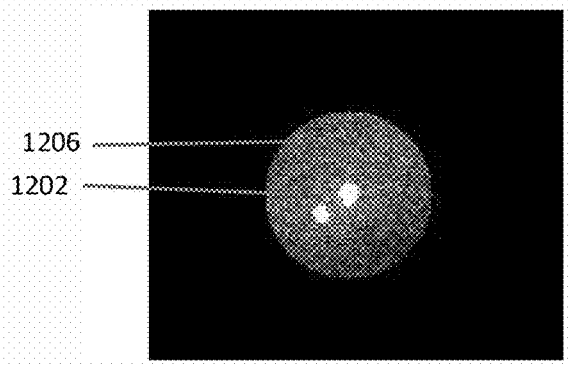
FIG. 12C    FIG. 12D
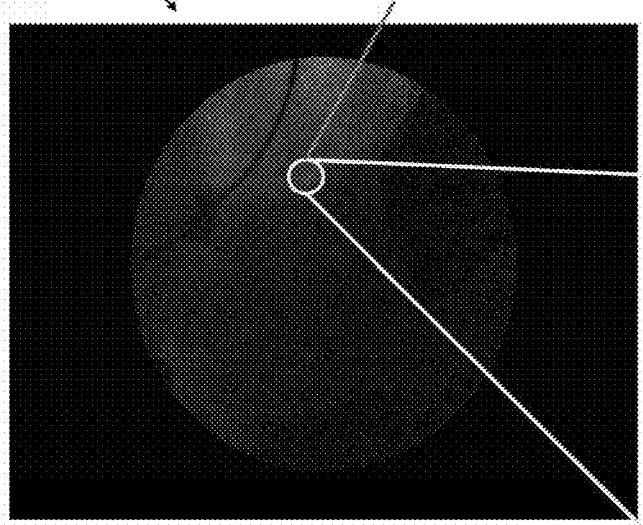 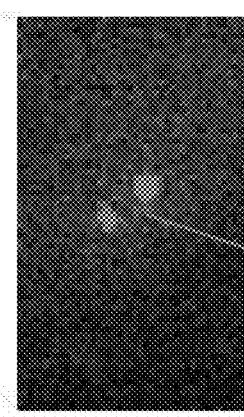
FIG. 13A    FIG. 13B

SYSTEM AND METHOD FOR RESIDUAL CANCER CELL DETECTION

BACKGROUND

More than one million cancer surgeries are performed each year in the United States and nearly 40% of them fail to remove the entire tumor according to the National Cancer Institute Surveillance Epidemiology and End Results report. Situations in which cancer cells were left behind in the patient can result in secondary surgeries. For example, in breast cancer lumpectomies, failure to remove all of the cancer cells during the primary surgery occurs approximately 50% of the time and requires second surgeries. Such secondary surgery or multiple surgeries create increased rates of cancer recurrence and reduce long term survival of the patient.

Typically, after a solid tumor resection, the surgeon removes the bulk of the tumor and sends it to a pathologist for post-operative assessment of the resected tumor tissue to determine whether residual cancer was left behind in the patient. However, this pathology assessment is a time intensive procedure and often takes days for final results to be sent to the surgeon. Should the pathologist indicate in the pathology report finding of a portion of the removed tissue with cancer cells bordering the edge (a diagnostic term known as "positive margin"), additional resection may be required to complete removal of the residual cancer cells in the patient and in the situation after the patient has completed the initial surgery, this finding may require the surgeon to perform a second surgery.

SUMMARY

Various aspects of the present application relate to in situ observation of residual cancer cells in a tumor resection bed during cancer surgery. For example, there exists an imaging technology that includes a probe that fluoresces upon activation by a target cell and a hand-held fluorescence imaging device in order to allow for intraoperative identification of residual cancer in order to reduce the need for follow up surgeries and minimize the potential for recurrence. See, for example, U.S. patent application Ser. Nos. 14/211,201 and 14/211,259, the disclosures of which are incorporated herein by reference in their entirety. In situ observation techniques may typically provide an intraoperative surgical site image with cancer cells marked with an imaging agent against a background. The background of the surgical site image may include healthy tissues. Imaging the healthy tissues in the field of view of the surgical site image may facilitate the surgeon in locating the surgical site during operation, while the cancer cells highlighted with an imaging agent in the image may help the surgeon identify residual cancer to be removed. It is appreciated that there remains a need for detecting residual cancer cells during surgery in order to insure that all of the cancer has been removed from the tumor-bed. The present application is directed to a method and system for performing image analysis for identification of residual cancer cells in a tumor resection bed. Further, the system and methods discussed herein may be used to detect pre-cancerous conditions as well.

According to some embodiments, a method for detecting cancer cells is provided. The method comprises the acts of collecting a surgical site image; indicating, on a display, one or more locations of the detected cancer cells. The cancer cells are residual cancer cells remaining after an initial surgery. Indicating the one or more locations of the detected cancer cells comprises acts of determining and selecting a portion of the surgical site image responsive to an intensity parameter; modifying the selected portion of the surgical site image to determine one or more groups of residual cancer cells based on size; identifying at least one of the one or more groups of residual cancer cells from the modified portion of the surgical site image using a local-based threshold and displaying the identified at least one of the one or more groups of residual cancer cells on the display.

According to some embodiments, at least one non-transitory computer-readable storage medium is provided. The non-transitory computer-readable storage medium comprises computer-executable instructions that, when executed by at least one processor of an image analysis system configured to collect a surgical site image, perform a method to detect abnormal cells in a surgical site. The method comprises determining and selecting a portion of the surgical site image responsive to an intensity parameter; modifying the selected portion of the surgical site image to determine one or more groups of abnormal cells based on size; identifying at least one of the one or more groups of abnormal cells from the modified portion of the surgical site image using a local-based threshold and indicating, on a display, the identified at least one of the one or more groups of residual cancer cells.

According to some embodiments, a computer-implemented method is provided for identifying residual cancer cells after an initial surgery to an operator of a residual cancer cell detection system. The residual cancer cell system has a display and a medical imaging device. The method comprises presenting, in the display, a surgical site image from the medical imaging device to the operator; presenting, in the display, an input component that allows the operator to provide at least one parameter to the residual cancer cell detection system; accepting, in the display, the at least one parameter provided by the operator; and presenting, in the display, to the operator, a result of a residual cancer cell detection performed by the residual cancer cell system using the at least one parameter.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 10B is a slice of data plot showing cross-sectional signal intensity values along the pixels on a horizontal line FIG. 10A. FIG. 10D is a slice of data plot showing a cross-sectional signal intensity value along the pixels on a horizontal line in FIG. 10C;

FIGS. 12A-D show images used to perform local contrast based filtering on the identified features according to an exemplary embodiment. FIG. 12A and FIG. 12C show the same region for two bright spot features as in FIG. 12B and FIG. 12D, except with the pixels for the two bright spot features removed;

FIGS. 13A-B show a modified input image and an enlarged area of the input image, respectively, containing the two cancer cell features identified using image analysis according to an exemplary embodiment.

DETAILED DESCRIPTION

The inventors have recognized and appreciated that in order to improve the efficacy of cancer surgeries, it is desirable to have a system that can identify from surgical site images abnormal cells such as residual cancer features that are mm to sub-mm in size and/or not easily identified with traditional visual inspection. For some of these small residual cancer types, simple signal thresholding methods may lack the specificity required by surgeons to adequately identify residual cancer cells. In some embodiments, an approach for identifying these features would consider not only the absolute brightness of the feature, but its size and local contrast as well. Described herein are systems and methods to identify small residual cancer features that can be used with in situ observation techniques. In some embodiments, the methods include a process for detecting small residual cancer features when paired with an intraoperative imaging methodology using a handheld imaging device. In some embodiments, the small residual cancer features are imaged with limited brightness due to physiological effects that may limit the amount of activated imaging agent present at the feature in question.

Figure 1:
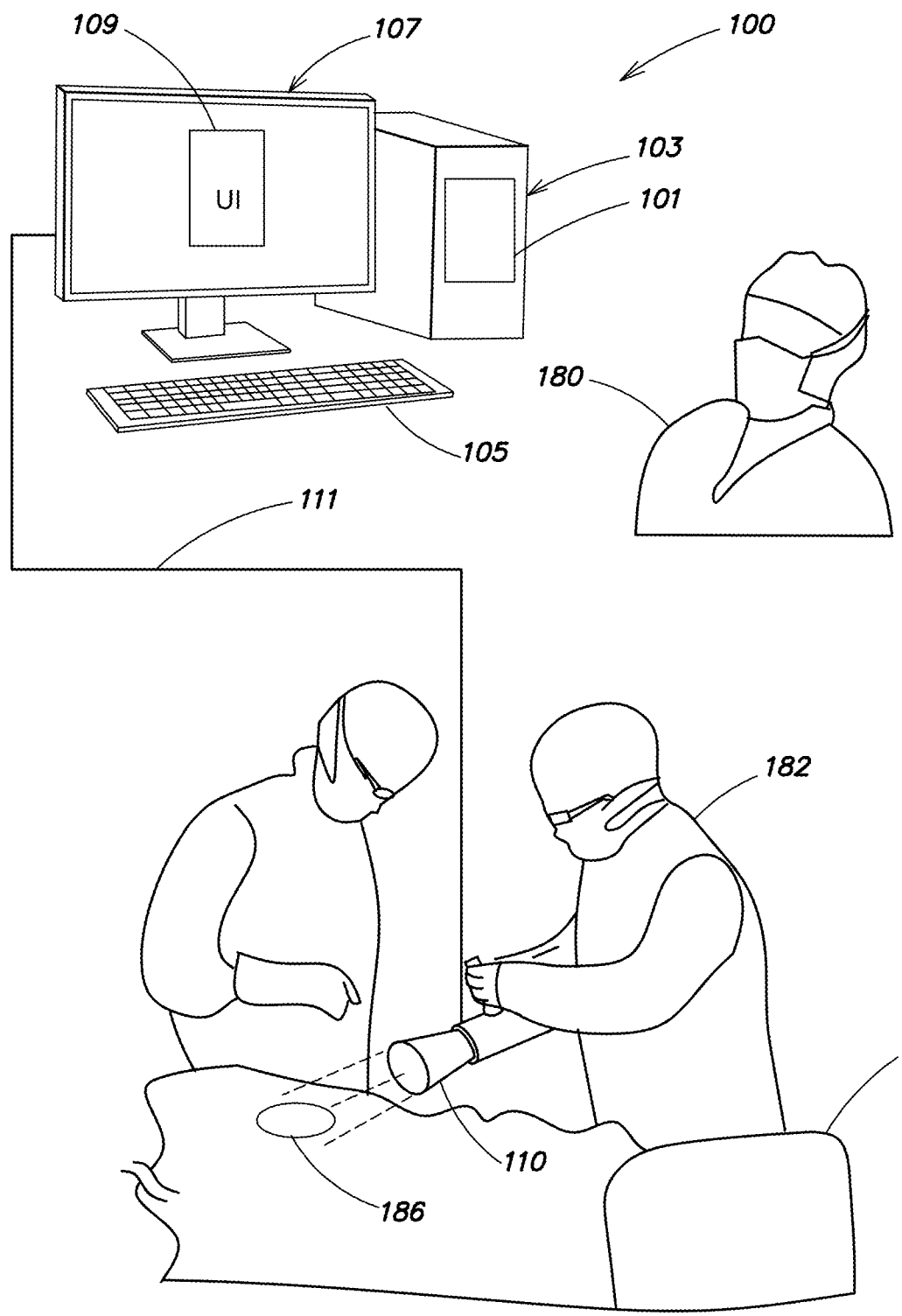
FIG. 1 is a schematic diagram showing an overview of components of an exemplary system for identifying residual cancer cells after surgery according to some embodiments.

FIG. 1 is a schematic diagram showing an overview of components of an exemplary system 100 for identifying residual cancer cells after surgery, according to an embodiment of the present application. An operator 180 may use one or more input devices 105 to interact with a User Interface (UI) 109 to issue commands and/or queries associated with an image analysis system 101. The image analysis system may be implemented using a computer-based hardware element 103 that is specially programmed to process one or more images in order to identify residual cancer features in the images. The output of the image analysis system may be presented on a display device 107 to the operator within the operating room environment.

In some embodiments, the images are captured by one or more surgeons 182 during or after a tumor resection surgery on a patient on surgical bed 184. The images may be captured in-situ at the surgical site 186 where the tumor is resected using a medical imaging device 110 and transmitted in real-time to the image analysis system 101 via a data connection 111. Used in this scenario, the system 100 is able to provide a real-time feedback on the size and location of residual cancer cells remaining in the surgical site after the resection surgery is performed. In some cases the image analysis results provided to the operator 180 may facilitate the surgeon 182 in performing residual cancer cell removal procedures on the patient and obtain further confirmation from the image analysis system that all remaining cancer cells in the surgical site 186 are completely removed, without the need for a second, separate residual cancer cell removal surgery.

Figure 2:
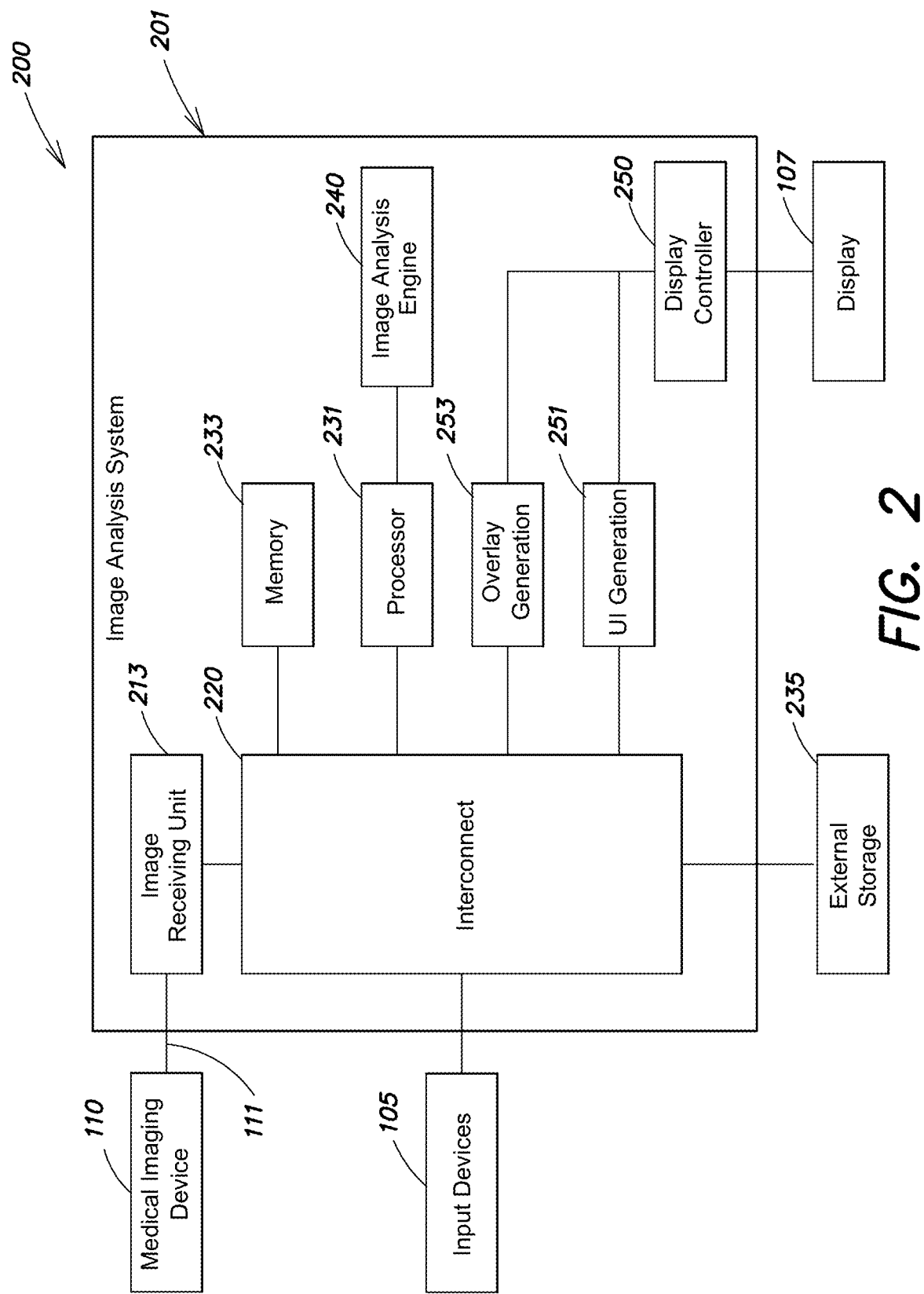
FIG. 2 is a block diagram of another exemplary cancer cell detection system according to some embodiments.

FIG. 2 is a block diagram of a cancer cell detection system 200 that is an example of the system 100 of FIG. 1. Some of the components are the same and thus the same reference numbers are used. In the example in FIG. 2, the image analysis system 201 includes an interconnect 220 used to interface with and coordinate with various different components in the system. The interconnect 220 may comprise one or more digital buses or any other type of suitable interconnections that allow high speed communication of digital data between a plurality of interconnected components. In some embodiments, the interconnect 220 interacts with processor 231 to process image data received from an image receiving unit 213 and obtains from the processor 231 the image analysis results in order to provide the image analysis results to an external display 107 for the operator 180. In some embodiments, the interconnect 220 may communicate non-image data with the processors. For example, processor 231 may receive programming instructions from the interconnect 220 in order to execute a series of methods on the processor. In some embodiments, the interconnect 220 communicates with a memory 233 to store and read image and non-image data for the processor. For example, memory 233 may be a computer memory that stores program instructions executable by the processor 231 that when executed by the processor 231, perform one or more methods to identify residual cancer cell features from images. It should be appreciated that any suitable computer readable storage media may be used in the image analysis system as memory 233 for storage of image data and program instructions.

According to some embodiments, processor 231 may additionally communicate with an image analysis engine 240 in order to process image data to identify residual cancer cell features. As will be discussed in detail below in connection with FIG. 4, image analysis engine 240 may include one or more units each specialized for executing instructions for image enhancement and analysis. In some embodiments, the units in image analysis engine 240 may be integrated on a single chip together with processor 231 in order to reduce packaging dimensions, power consumption and manufacturing cost. In some other embodiments, image analysis engine 240 may be implemented on discrete processing chips specialized in performing high speed image processing such as a graphics co-processor or a field programmable gate array (FPGA). Further, one or more image analysis features may be incorporated within the medical imaging device (e.g., device 110).

In the system in FIG. 2, display controller 250 receives the image analysis results from the processor 231 via interconnect 220 and provides one or more processed images indicating the size and location of the detected cancer feature to an external display 107 for the operator 180. In some embodiments, an overlay generation unit 253 generates an overlay and/or highlighting based on the image analysis results to be provided to the display controller such that the overlay and/or highlighting are presented to the operator 180 to accentuate the identified cancer features on the display 107.

In the system in FIG. 2, medical imaging device 110 is used to capture intraoperative images of the patient's surgical site and to transmit the captured image data to the image receiving unit 213 via a data connection 111. The captured image data may be stored in memory 233 and subsequently processed by processor 231 and image analysis engine 240 to identify residual cancer features in the image data. It should be appreciated that multiple image data may be captured by the medical imaging device, stored in memory 233 and processed by the processor 231 and image analysis engine 240 for output to display 107 in substantially the same period of time in order to provide real-time feedback of the size and location of residual cancer cells to the operator. For example, the medical imaging device 110 may capture images at a specific video rate (e.g., 10 frames per second, 12 frames per second, 24 frames per second or 30 frames per second) and transfer the video rate images for processing and output as real-time video features at substantially the same rate on display 107 in order to facilitate the surgeon's operation in removal of identified cancer cells.

In some embodiments, the medical imaging device 110 may be a handheld imaging device. In one non-limiting example, the handheld imaging device may be a hand-held fluorescence imaging device with a photosensitive detector sensitive to fluorescence signals corresponding to a photons emitted from fluorescence of certain fluorescent imaging agent with which the cancer cells are labelled with. In some embodiments, the imaging device may also include an excitation source that is configured to emit excitation wavelengths of particular fluorescent imaging agent towards the object or surgical bed being imaged. A description of an example hand-held fluorescence imaging device may be found in U.S. patent application Ser. No. 14/211,201 titled "MEDICAL IMAGING DEVICE AND METHODS OF USE", filed on Mar. 14, 2014, the disclosure of which is incorporated herein by reference in its entirety. Of course, while a handheld device is mentioned above, the systems and methods described herein are not limited to only use with a handheld device. Instead, they may be implemented on any appropriate imaging and/or analysis system regardless of size scale.

According to some embodiments, images captured in a handheld imaging device may comprise pixels with brightness or intensity levels that correspond substantially to the number of fluorescent photons emitted from portions of tissues being imaged in the surgical site. The intensity value of each pixel on the captured image is substantially proportional to the number of fluorescently labelled cancer cells in a portion of the tissue within the total field of view of the imaging device. The size and location of a pixel relative to the captured image correspond to the size and location of the portion of the tissue relative to the total field of view in the imaging device. Images transmitted from the medical imaging device 110 to the imaging receiving unit 213 may include a high number of pixels in each one of two orthogonal directions in an array, such that the size of the portion of the tissue corresponding to a pixel, or in other words the corresponding field of view for a single pixel, is no bigger than a size representing a desired spatial resolution of the imaging device. Without wishing to be bound by theory, a typical cancer cell may be on the order of approximately 15 µm across. The medical imaging device may be configured such that a field of view of each pixel may be equal to or greater than about 1 µm, 2 µm, 3 µm, 4 µm, 5 µm, 10 µm, 15 µm, 30 µm, or any other desired size. Additionally, the field of view of each pixel may be less than about 100 µm, 50 µm, 40 µm, 30 µm, 20 µm, 10 µm, or any other desired size scale.

In one specific embodiment, the field of view per pixel may be between about 5 µm and 100 µm inclusively. In another embodiment, the field of view per pixel may be between about 5 µm and 50 µm inclusively. Having the field of view of each pixel being on the same order in size or smaller than each cancer cell leads to enhanced resolution and contrast for labeled cancer cell features in the surgical site image, as each cancer cell is covered by one or more whole pixels with high fluorescent intensity against a background with much lower intensity. Such high resolution and contrast allows the system to identify small features with only a handful of cancer cells from surgical site images that are not easily identified with traditional visual inspection means. Of course pixels with fields of view both larger and smaller than those noted above are also contemplated, as the disclosure is not so limited. Further, such an imaging capability may permit detection of certain types of cancer cells having a particular shape and/or geometry. It is appreciated that particular cancer cells have a particular fundamental geometry and therefore such geometries may be stored in a memory, compared to sampled geometries and detected by the system.

In some embodiments, each image captured by the medical imaging device 110 comprises an array of pixels each with a digitized intensity value representing the concentration of imaging agents at the corresponding field of view of the pixel. In one example, the intensity value for each pixel is sampled and is digitized with 12-bit resolution. In other examples, the digitization resolution may be other resolutions such as 8-bit, 14-bit, 16-bit, or any suitable resolution for recording and transmitting the image. The captured images are transmitted from medical imaging device 110 to the image receiving unit 213 via data connection 111. In some embodiments, raw, uncompressed image data are transmitted to ensure integrity of the image, although it should be appreciated that any suitable data compression technique and format may be used to enhance the image data transmission rate from the medical imaging device 110.

Besides image data, the data connection 111 may also transmit non-image data from the medical imaging device 110 to the image analysis system 201. In one embodiment, image scaling information may be transmitted accompanying each surgical site image in order for the image analysis system to convert pixel size into units of length measurement such as mm or µm. In some embodiments, the converted sizes of one or more groups of pixels may be compared with a known threshold value based on cancer cell sizes and/or geometries in order to identify the one or more groups of pixels as cancer cells in the surgical site image.

Additionally, the data connection 111 may transmit non-image data from the image analysis system 201 to the medical imaging device 110. Such non-image data may be used, for example, by the operator 180 to control the medical imaging device to perform image capture, transmission, adjustment of magnification/total field of view and/or as focusing depth of the optical system within the medical imaging device to provide a full survey of the surgical bed for residual cancer cells after the initial tumor resection.

In some embodiments, operator 180 as shown in FIG. 1 may use one or more input devices 105 to interact with the image analysis system. In the embodiment in FIG. 2, input devices 105 are coupled to the interconnect 220 to route commands and queries from the operator to various components of the system. The input devices may include a keyboard for typing text, a mouse to interact with one or more screen objects on the UI 109 on the display 107 as shown in FIG. 1. For example, the operator may type in annotation texts accompanying the received surgical site image or the analyzed residual cancer cell results. The operator may use the input device to reconfigure the UI 109, interact with UI 109 to adjust settings on the medical imaging devices and/or image analysis settings such as one or more threshold values depending on the type of cancer cells being treated. In some embodiments the input devices may also include a stylus-sensitive or a finger-sensitive touch screen, external or integral to the display 107. It should be appreciated that any suitable human interface device may be used for the operator 180 to provide commands and queries to the system. In some embodiments the input devices may include gesture controls or voice controls. In another embodiment, the input devices may additionally provide audio, visual or tactile feedback to the operator to indicate one or more characteristics in relation to the input command and/or queries.

In some embodiments, the image analysis system 201 in FIG. 2 may include a UI generation engine 251 adapted to generate screen objects for the display controller 250 to present on the display 107 as the UI for interacting with the operator. The UI may be generated based on instructions stored in memory 233 and may be dynamically adjusted based on user input from input devices 105.

The system 200 in FIG. 2 may also include external storage 235 connected to the interconnect 220, configured to store both image data and non-image data, for example, for archival purpose. In some embodiments, program instructions may be read from and stored on the external storage 235.

As discussed above, aspects of the present application relate to methods for detecting cancer cells, such as those remaining in a surgical site after removal of bulk tumors, in order to facilitate complete removal of residual cancer cells.

Figure 3:
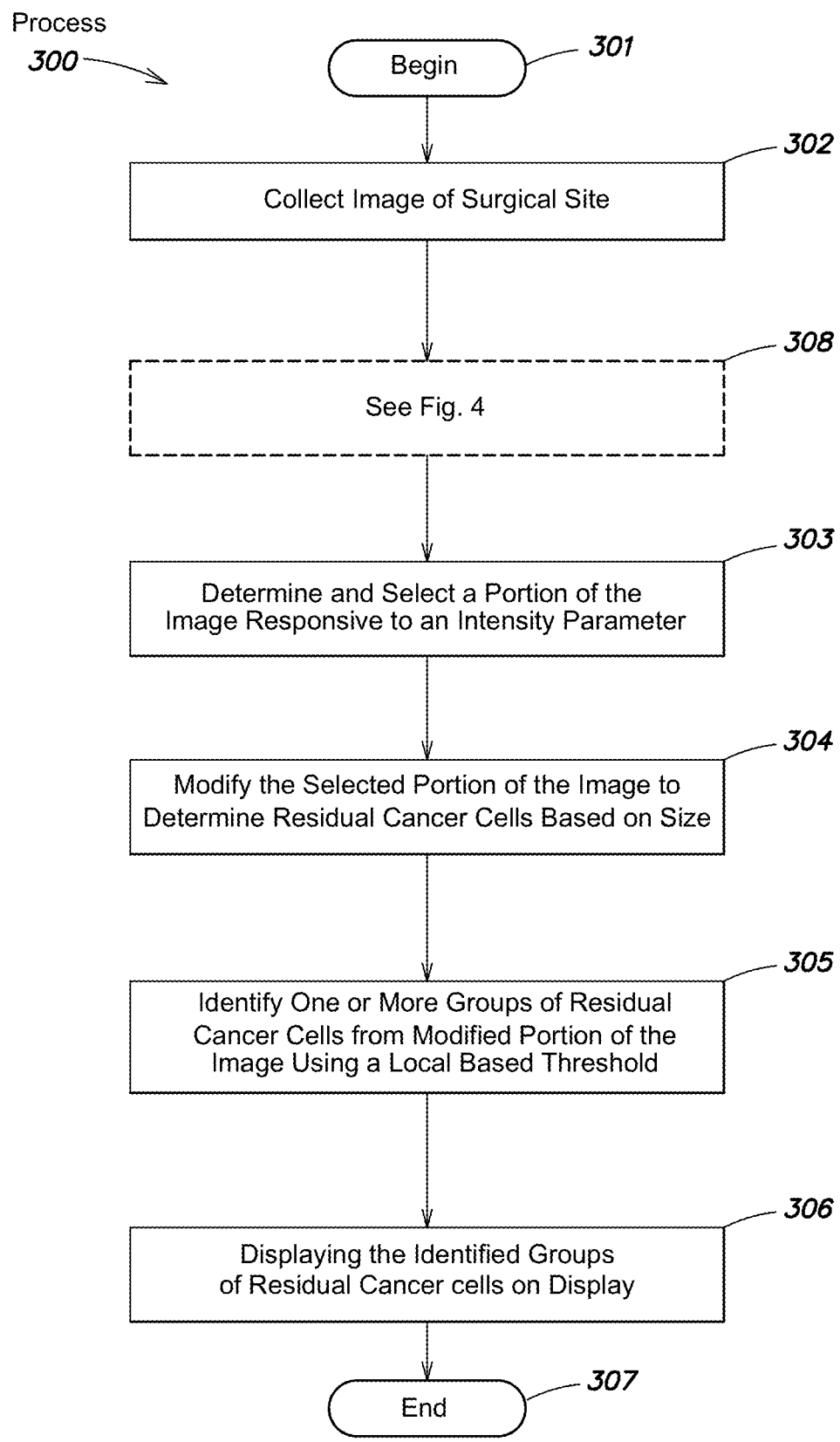
FIG. 3 is a flow chart showing an exemplary process for detecting residual cancer cells according to some embodiments.

FIG. 3 is a flow chart showing an exemplary process 300 for detecting residual cancer cells according to some embodiments. After the process begins at block 301 in FIG. 3, at block 302, images are captured at the surgical site using, for example, a handheld imaging device. In some embodiments, the surgical site images may be still images and/or videos containing images captured at a particular video rate.

At block 303, a portion of the collected image is selected based on a comparison between a characteristic of the pixels in the portion of the image with a predetermined characteristic threshold. In one non-limiting example, the portion of the image may be selected for further analysis after a determination that the intensity parameter for each pixel in the portion of the image exceeds a threshold value corresponding to a simple brightness threshold expected for a given type of cancer cell labeled with an imaging agent. One goal for performing a selection process based on simple thresholding is to exclude background pixels representing light emission from healthy tissues from further analysis. The inventors have recognized that in some embodiments, even though fluorescent imaging agents are configured to selectively bind to cancer cells, finite fluorescence intensity may still appear in pixels corresponding to non-cancer cell regions in the surgical site.

In some cases, the finite background intensity may be due to background noise in the photodetector or in the circuitry of the medical imaging device. The finite background intensity may also arise from fluorescent signals emitted from a small amount of imaging agents with non-specific binding in the healthy, non-cancer cell regions. Therefore in some embodiments, relying on a simple threshold determination alone may not be sufficient to prevent false positive identification of cancer cell regions, weed out background tissues and accentuate substantially only cancer cells from the images.

Subsequently at block 304, the portion of the collected image selected at block 303 is modified to identify one or more groups of residual cancer cell features against background based on size. For example, features in the selected portion of the image may be discarded or excluded if representative sizes of the features are determined to be outside a size range associated with the cancer cell type targeted for removal. As used herein, feature size should be understood to refer to a properly scaled size dimension of a region of tissues on the surgical site as measured in, e.g., mm or µm, that corresponds to the feature on the surgical site image.

At block 305, the one or more groups of residual cancer cells identified at block 304 are further filtered using a local based contrast method, as will be discussed in detail below. In some embodiments, a local contrast is determined for each group of residual cancer cell features based on a comparison between signal intensity of pixels substantially within and outside the feature. Only features with contrast above a predetermined threshold are identified as cancer cells in order to distinguish against the background and reduce false positive identifications.

The identified cancer cells according to blocks 303, 304 and 305 are presented to a display (such as display 107 in FIG. 1) to operator 180 at block 306 before the residual cancer cell identification process ends at block 307.

Figure 4:
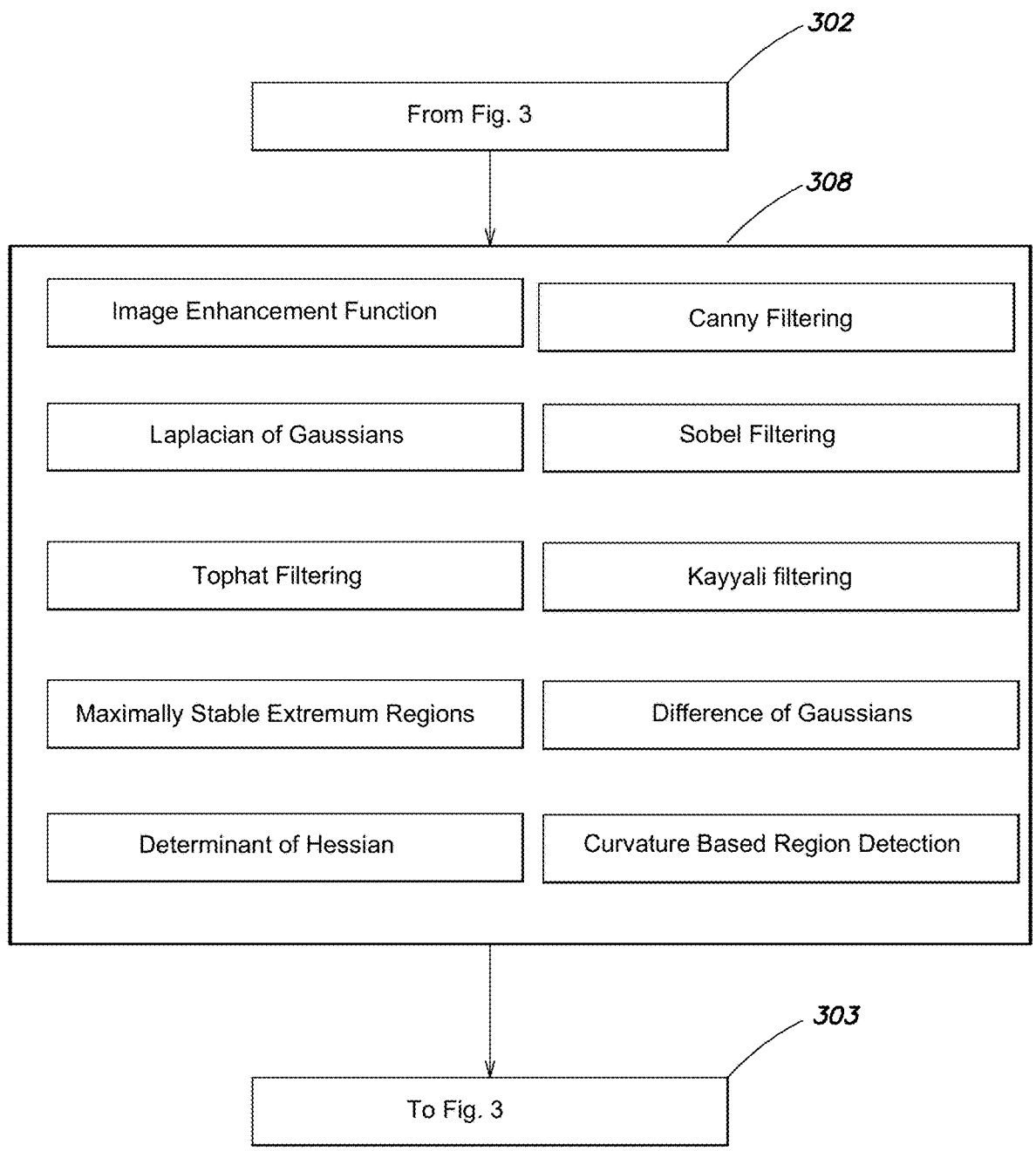
FIG. 4 is a block diagram showing an exemplary image enhancement process according to some embodiments.

In some embodiments, an image enhancement process may optionally and additionally be provided in the process 300 as shown in FIG. 3. FIG. 4 is a block diagram showing an exemplary image enhancement process at block 308. In FIG. 4, the images collected at block 302 in process 300 are enhanced at block 308. Enhancing the image may help remove noise and artifacts unrelated to the cancer cell features and improve the signal noise ratio of the cancer cell signals against background. Image enhancement at block 308 may be performed with one or more methods selected from the group comprising Canny Filtering, Sobel Filtering, Kayyali filtering, Principle Curvature-Based region detection, features from accelerated segment testing, Forstner filtering, a Laplacian of Gaussians, Tophat filtering, Difference of Gaussians, maximally stable extremum regions, and a determinant of Hessian. Each one of the image enhancement method in the above group is a blob detection method aimed at detecting regions in a digital image with different properties compared to surrounding regions. It should be appreciated that any suitable number and combination sequence of blob detection methods for enhancing a gray scale image may be used at block 308. The enhanced images are passed to the process at block 303.

In some embodiments, each of the process blocks 303 to 305 and 308 as illustrated in the block diagrams in FIG. 3 and FIG. 4 may be applied individually or selectively in groups of any suitable combination sequence depending on the type of tissue and/or residual cancer cell types being targeted.

Figure 5:
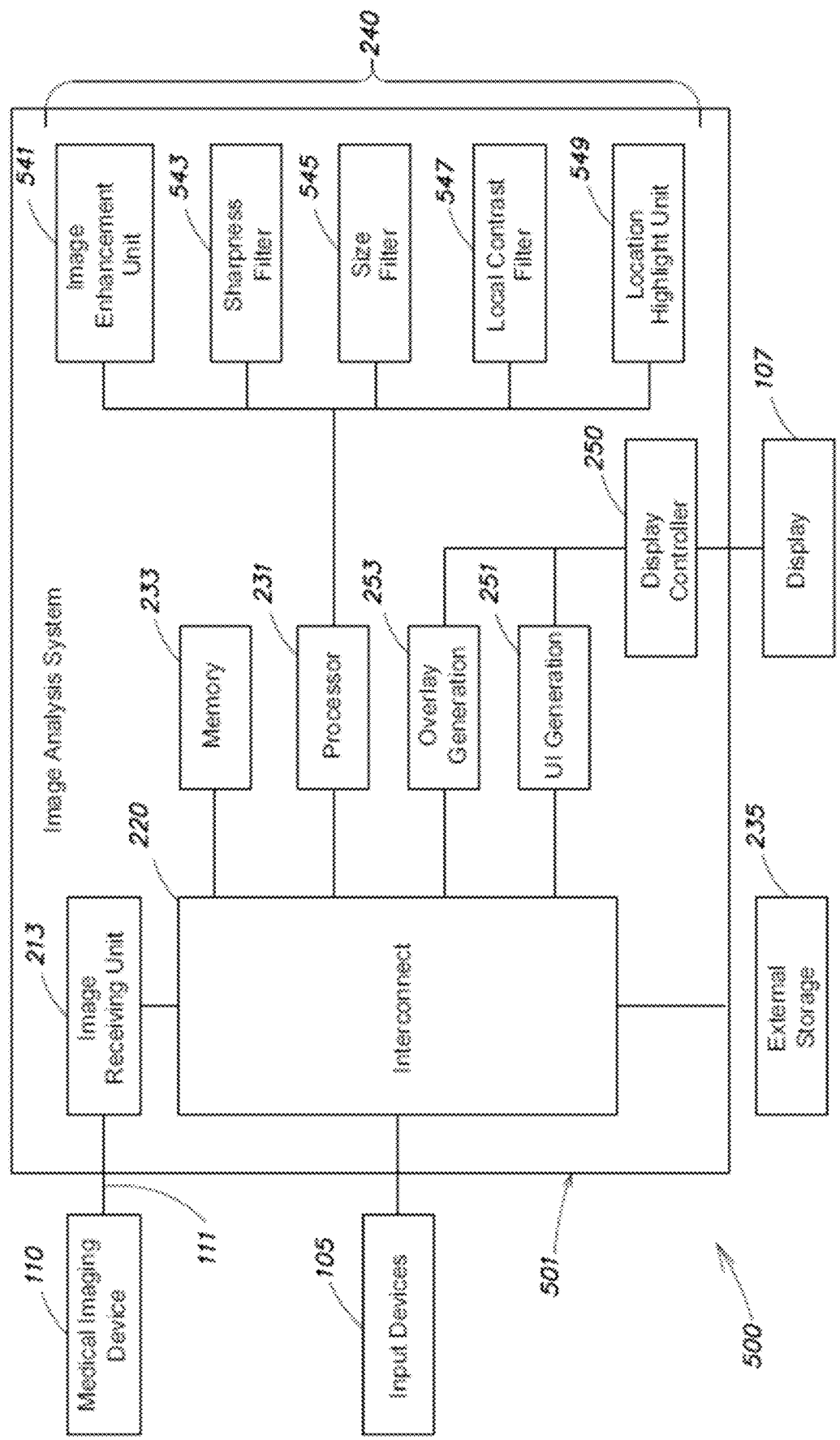
FIG. 5 shows a block diagram of an exemplary cancer cell detection system according to some embodiments.

In some embodiments, the exemplary process 300 shown in FIG. 3 and FIG. 4 may be performed by the system 200 in FIG. 2 sequentially to process images received by the image receiving unit 213 from the medical imaging device. FIG. 5 shows a block diagram of an exemplary cancer cell detection system 500 that is, in some aspects, similar to the system 200 in FIG. 2. Some of the components are the same between FIG. 2 and FIG. 5 and thus the same reference numbers are used. Image analysis system 501 in the system 500 in FIG. 5 includes an image analysis engine 240 that comprises an image enhancement unit 541, a sharpness filter 543, a size filter 545, a local contrast filter 547 and a location highlight unit 549, in order to perform one or more image analysis steps according to the exemplary processes shown in FIG. 3 and FIG. 4 and described above.

In some embodiments, the images are processed at a rate that is substantially the same as the rate of images received from the medical imaging device. In some embodiments, videos containing surgical site images captured at a video rate are processed at substantially the same video rate such that the identified cancer cells in each frame of the videos are identified and presented as a video in the display 107. In another embodiment, processing of multiple images according to process 300 may be carried out in parallel during substantially the same time period using processor 231 and/or the image analysis engine 240. Such multi-threaded parallel processing may generally increase the speed of cancer cell identifications, leading to accurate and prompt feedback to facilitate surgical removal of the residual cancer cells.

Figure 6:
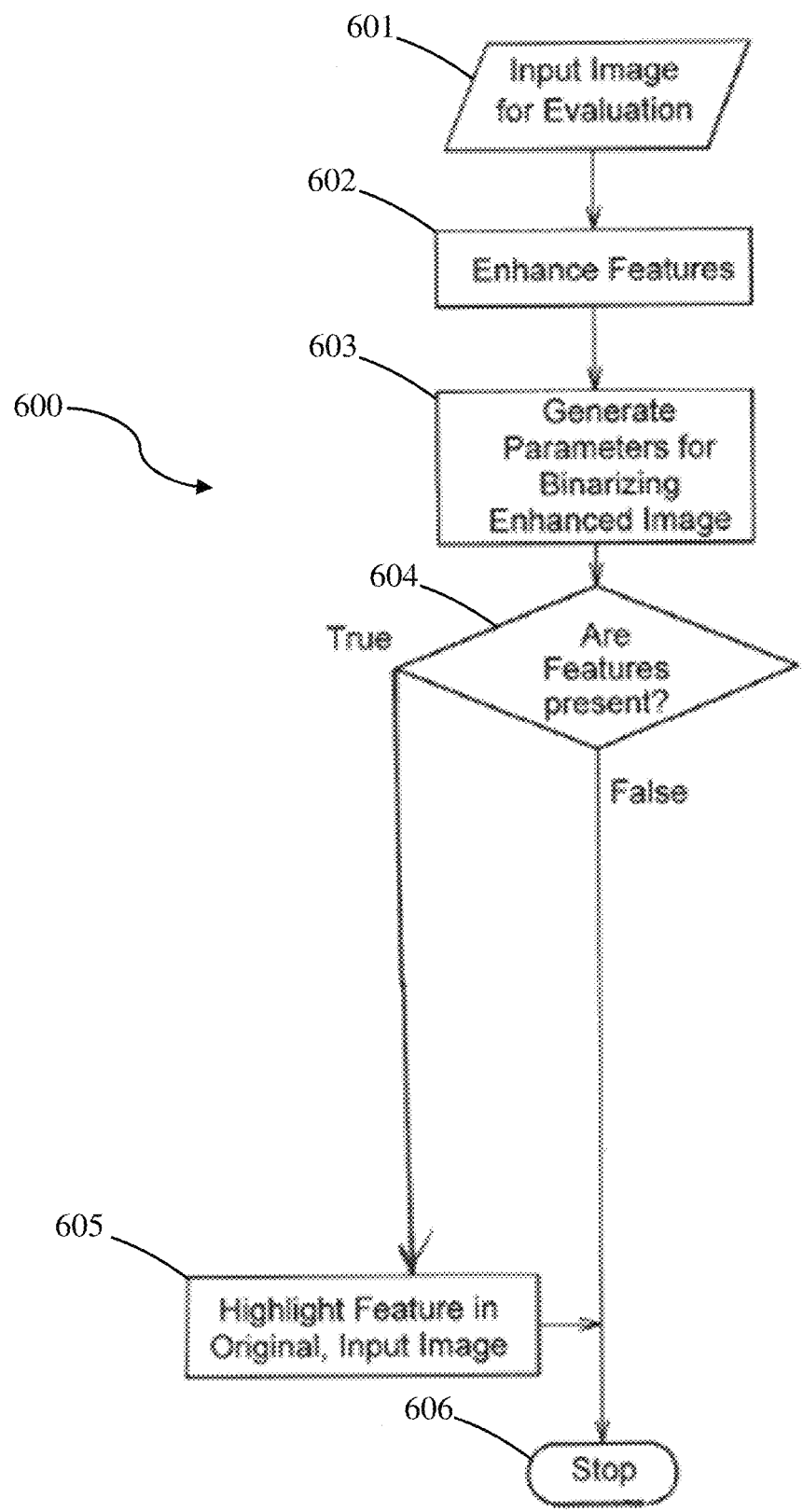
FIG. 6 is a flow diagram showing another exemplary process for detection of cancer cells based on images from a medical imaging device according to some embodiments.

FIG. 6 is a flow diagram showing another process 600 for detection of cancer cells based on images from a medical imaging device according to an embodiment. Features in the image collected at block 601 are first enhanced at block 602 using one or more image enhancement processes similar to those discussed above in relation to block 308 in FIG. 4.

In some embodiments, the system may filter the enhanced image received from block 602. A detection process may be trained to determine filter settings using identified cancer images. Comparisons between healthy and non-healthy tissue may be used to set parameters (e.g., train) the detection process to identify residual cancer cells in the image.

In some embodiments, the detection settings may be adjustable either as a result of program instructions or based on operator input at the UI in order to optimize the detection process. In one example, the enhancement features include a blob detection method that improves the sharpness of the image.

At block 603, parameters are generated for binarizing the image into background pixels and relevant, contiguous features to create an enhanced image. For example, features in the enhanced image with a parameter that identifies a feature within the enhanced image (e.g., determined by true condition obtained at block 604 of FIG. 6) may correspond with substantially more confidence to cancer cells and are passed to subsequent processes for further analysis. Such features may be determined at block 604 as being present or not within the enhanced image.

Conversely, features that do not have the identified parameter(s) (e.g., determined by false condition obtained at block 604 of FIG. 6) may be deemed background or non-cancer features. The process proceeds to stop 606. It should be appreciated that process 600 may be repeated for additional images or portions of the images (e.g., responsive to a user input, magnification of the currently-viewed image, etc.).

Features in the image that are determined as true at block 604 may be further evaluated according to a size filter. In some embodiments, features outside a size range associated with the cancer type being targeted may be discarded. In one example, size may be determined based on 4-connected or 8-connected objects in which all pixels in an object are above a threshold. In some embodiments, the size range may comprise an upper and a lower size limit (M and N, respectively) that define acceptable feature dimension. Acceptable sizes may be determined based on historical data that is collected and stored by the system, and compared to measurements made in situ.

Features in the image that are determined as true for fitting within the size range may be further evaluated according to a local based contrast filter. In some embodiments, the pixels identified based on thresholding the enhanced image and filtering for size are evaluated for local contrast in the original input image. Contrast is calculated by defining a region of pixels surrounding the center of mass of a contiguous feature, and dividing the signal mean for the contiguous feature by the mean of the surrounding region. The surrounding region is defined by a geometric shape relative to the above threshold, contiguous feature. In some embodiments, the geometric shape may be a circle with fixed radius, or a square with a fixed side length, or any other suitable shape and dimensions. If a feature meets criteria established by the system, then the pixels in that feature, according to one embodiment, are assigned a "1" (e.g., as determined by true condition obtained at block 605 of FIG. 6), all other pixels are assigned a "0" value (e.g., as determined by false condition obtained at block 605 of FIG. 6).

In some embodiments, if a feature meets the criteria, its pixels are given a value of "1" for highlighting. Pixels with a value of "1" may receive a pseudo-color on top of the initial gray-scale image in order to draw a surgeon's attention to that feature. Additionally, the highlighted feature may receive geometric highlighting such as a circle drawn around it or an arrow pointing to it in order to direct the surgeon's attention to the location of the detected cancer cell features. In this way, an improved UI is provided for in-situ identification of suspect cells.

Figure 7:
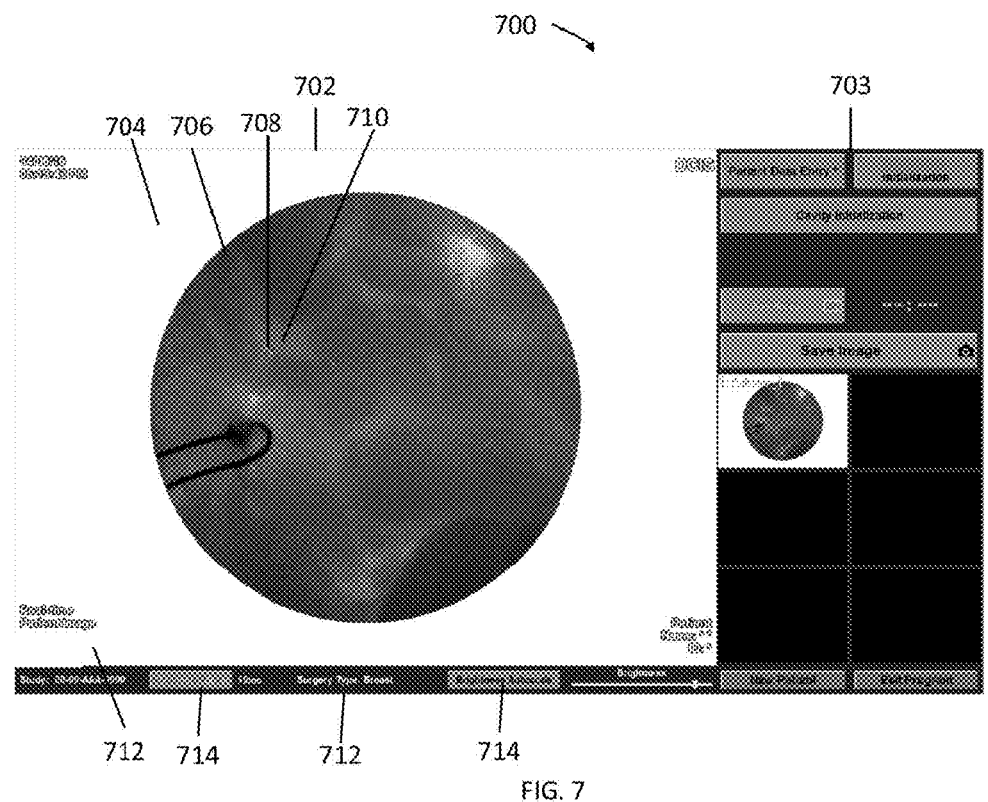
FIG. 7 is a screenshot image showing an exemplary user interface according to one embodiment that is configured to display identified cancer cell features to an operator.

FIG. 7 is a screenshot image showing an example user interface 700 according to one embodiment that is configured to display identified cancer cell features to an operator, such as operator 180 in FIG. 1. User interface 700 includes an image display window 702, which may be, for example, generated by the display controller 250 in the image analysis system 201 in FIG. 2 and presented on a portion of display 107 in order to display the image analysis results from processors in the image analysis engine 240. Referring back to FIG. 7, image display window 702 includes a main display area 704 where detection results of cancer cell features are displayed. In the example in FIG. 7, the main display area 704 shows an image captured by the medical imaging device 110 showing a total field of view of tissues in the surgical site 706. In some embodiments, the main display area 704 is updated substantially at the same rate of image capture from the medical imaging device 110 in order to provide near real-time visual feedback to the operator.

In one example, a surgeon performing a tumor resection operation may benefit from real-time in-situ visualization of the surgical site being operated on to assist with removal of cancer cell features, eliminating the need for secondary surgeries and the associated risks. A portion of the main display area 704 may be highlighted, such as with an unique color via pseudo-coloring 708 or with a geometric marker such as circle 710, in order to indicate the location of one or more detected residual cancer cell features based on the image analysis results from the image analysis system 201 as discussed in the sections above. Optionally and additionally, main display area 704 may include one or more data items 712, such as identification for the patent, the type of the surgery, the type of cancer, data and time, or any suitable information pursuant to the surgery. Data items 712 may also include graphical indications representing for example the brightness, size scale, zoom level and camera exposures. Further, the image analysis system 201 may also indicate, within the display area other information such as identified cell type, or any other measured or inferred parameter.

User interface 700 in FIG. 7 also includes a user control area 703 hosting a plurality of interactive controls responsive to an operator input through one or more input devices such as input devices 105 in FIG. 2. User control area 703 includes controls (e.g., buttons) to initiate actions such as capture image, initialize camera, save image to a storage device, save video to a storage device, begin new patient, exit the program, among other features. User control area 703 may also include controls that may launch further control elements. In the example in FIG. 7, a patient data entry control button is provided such that when selected, a text box control will be launched for the operator to enter patient data relevant to the surgery. In some embodiments, selecting the save image or save video control button may also launch an interactive window for the operator to select the file name and destination on the storage device for the image/video to be saved. User control area 703 may also include a list of previously saved images in preview images and/or text. In some embodiments, one or more controls may be provided for user to adjust the parameters used in the image analysis system 201, for example, the intensity threshold, multiplier, size threshold and local contrast threshold values that are optimized for the image analysis system 201 as disclosed in the sections above to perform cancer cell feature identification. In some embodiments, the optimized values are obtained from historical or empirical cancer cell identification results based for example on results from a control group of experiments. Controls that are used frequently may be placed directly in the image display window 702, in close proximity to the main display area 704. For example, control buttons 714 for adjusting brightness and exposure may be placed directly underneath the main display area 704.

The user interface 700 minimally performs one or more of the following functions, either above or in combination with other functions. The user interface presents in the display a surgical site image from a medical imaging device in a residual cancer cell detection system to an operator. The user interface presents, in the display, an input component that allows the operator to provide at least one parameter to the residual cancer cell detection system. The user interface accepts, in the display, the at least one parameter provided by the operator and presents, in the display, to the operator, a result of a residual cancer cell detection performed by the residual cancer cell system using the at least one parameter.

Having generally described embodiments for a system for identifying residual cancer cell features from intraoperative images and its methods of use above, several non-limiting examples of its application and implementation are provided below.

Example: Identification of Cancer Cell Features

Figure 8:
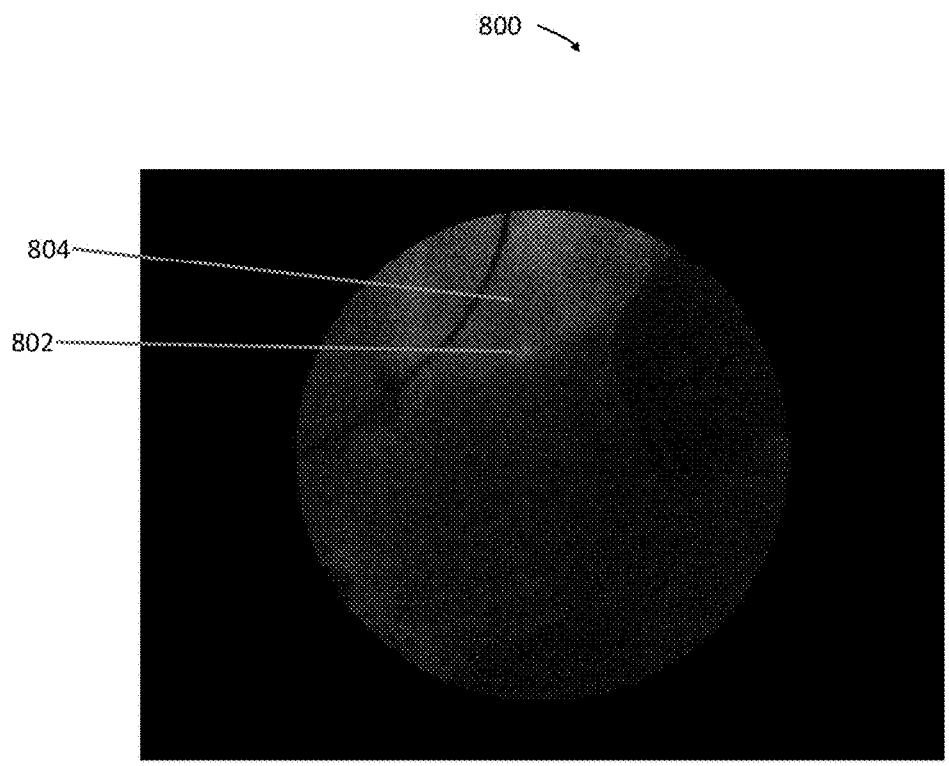
FIG. 8 is an image taken from a fluorescent imaging device according to an exemplary embodiment.

FIG. 8 is an image 800 taken from a fluorescent imaging device according to an exemplary embodiment. There are two bright dots 802 near the center of the image against a background 804. The image 800 in FIG. 8 is used as an input image for evaluation for residual cancer cells using a process similar to process 600 in the embodiment in FIG. 6.

Figure 9:
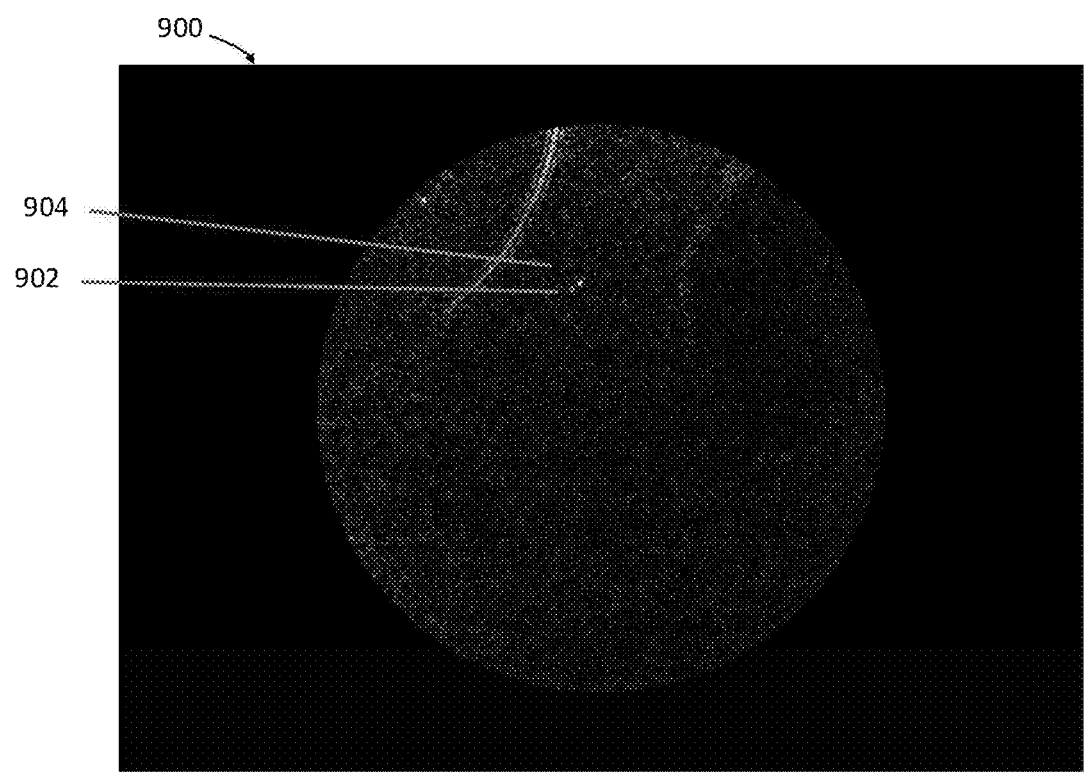
FIG. 9 shows an enhanced image after performing the method of feature enhancement according to an exemplary embodiment.

FIG. 9 shows an enhanced image 900 of the original input image 800 after performing the method of feature detection as detailed below. Image 900 in FIG. 9 is obtained by subtracting intensity values for each pixel in image 902 with corresponding pixels in image 904 and plotting the absolute value of the differences. The features 902 near the center of the image 900 are now much easier to identify as bright pixels against a dark background 904 with sharper edges around the features.

Figure 10A:
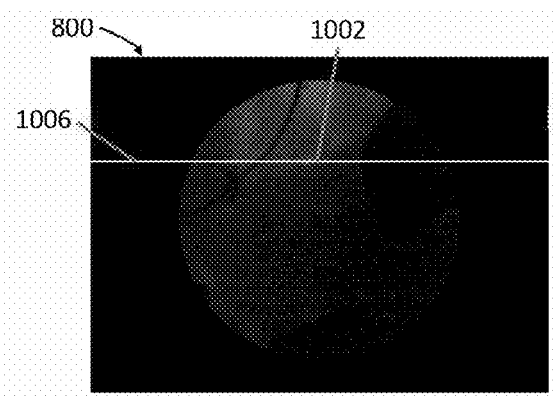
FIGS. 10A-D show panels of images and cross-section data illustrating the effectiveness of the image enhancement according to an exemplary embodiment.
Figure 10B:
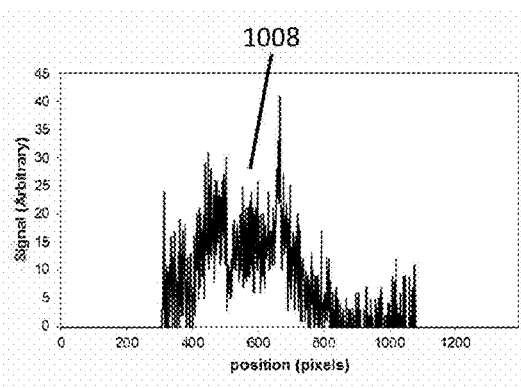
Figure 10C:
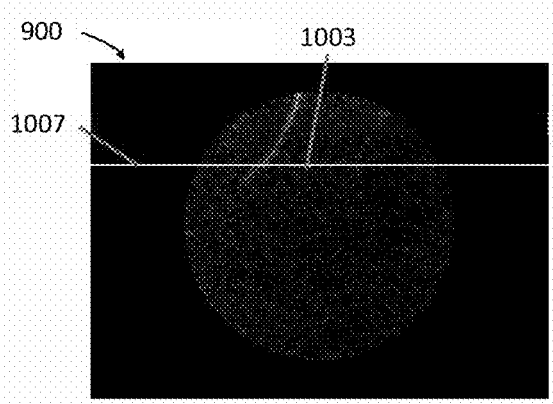
Figure 10D:
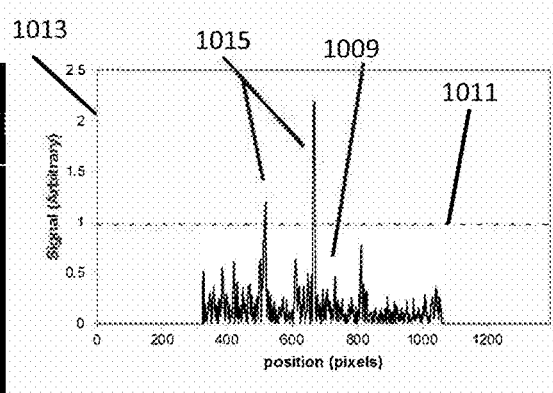

FIGS. 10A-10D show panels of images and cross-section data illustrating the effectiveness of the difference of image enhancement. FIG. 10A, which shows the original input image 800 with a white horizontal line 1006 through the location of the bright features 1002 identified near the center of the image. FIG. 10B is a slice of data plot 1008 showing cross-sectional signal intensity values along the pixels on the white horizontal line 1006 in FIG. 10A. Similarly, FIG. 10C, which shows the feature enhancement image 1000 from FIG. 10 with a white horizontal line 1007 through the location of the bright features 1003 identified near the center of the image. FIG. 10D is a slice of data plot 1009 showing a cross-sectional signal intensity value along the pixels on the white horizontal line 1007 in FIG. 10C. Comparing the cross-section data plots FIG. 10D with FIG. 10B shows that intensities of background pixels are suppressed and that intensities corresponding to the two bright spot features 1003 in the cross-sectional plot 1009 are enhanced compared to that in plot 1008.

Referring now to the cross-sectional signal intensity plot 1009 in FIG. 10D, a dashed horizontal line 1011 at an intensity value of around 1 on the vertical axis 1013 represents a cut-off intensity threshold. The threshold value is obtained by averaging intensity values of all pixels in the enhanced difference of image 1000 in FIG. 10, and multiplying the average with a multiplier. In the example in FIG. 10D, the multiplier is chosen as 1.6 to improve sharpness of the filtered features. Pixels essentially surrounding the two peaks 1015 in the cross-sectional plot in FIG. 10D have intensity values higher than the threshold dashed line 1013 and are chosen as the two features of interest for subsequent processing.

Figure 11:
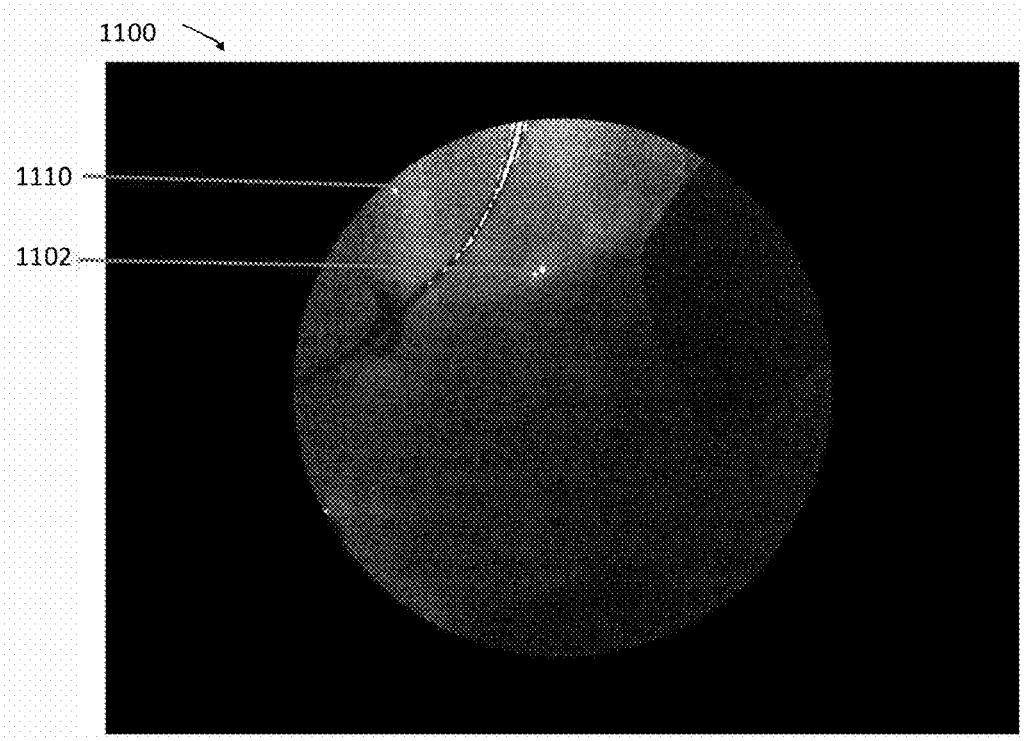
FIG. 11 shows a processed image after the feature enhancement and the intensity threshold filtering according to an exemplary embodiment.

FIG. 11 shows a processed image 1100 after the difference of enhancement and the intensity threshold filtering. The two bright features near the center of the image 1102 comprise pixels with intensity values that fall above the intensity threshold and appear as sharp and white features. FIG. 11 also shows a continuous curve feature 1110 from an imaging artifact unrelated to cancer cells. In fact, the curved feature 1110 exhibit dark or low fluorescent intensity closer to the background than to the expected fluorescent signals from cancer cells based on the original input image 800 in FIG. 8. Size filtering is performed to exclude artifacts such as feature 1110. Size for each filtered feature is determined based on 4-connected or 8-connected method in which all pixels with at least 4 neighboring or 8 neighboring pixels with intensity that fall above the intensity threshold are grouped together. Features such as the curve feature with sizes outside a range for typical cancer cells of a particular type are excluded from further evaluation.

For example, according to one embodiment, the system may be adapted to detect particular cancer and pre-cancerous cells. In one embodiment, The system may store parameters indicating particular size and geometries of certain indicated cancers and pre-cancerous indications including, but not limited to invasive ductal carcinoma, invasive lobular carcinoma, ductal carcinoma in situ, ovarian cancer, metastatic ovarian cancer, brain metastases, peritoneal carcinomatosis, esophogeal cancer, Barrett's esophagus, colorectal polyps, colorectal cancer, melanoma, basal cell skin cancer, squamous cell skin cancer, prostate cancer, lung cancer, sarcoma, endometrial hyperplasia, endometrial cancer, and cervical dysplasia, among other types.

FIGS. 12A through 12D show images used to perform local contrast based filtering on the identified features. Since fluorescently labeled cancer cells are expected to be much brighter than the non-cancer background, contrast thresholding may help select features that meet a certain contrast threshold as cancer cells while relegating features with not enough contrast as artefacts or non-cancer cell features.

FIG. 12B and FIG. 12D, a small circle 1206 highlights the portion of the original input image 800 selected for analysis containing two bright spots 1202 corresponding to the two features that exceed the intensity threshold and the size threshold for screening cancer cell features (see e.g., features 1015 and 1003 in FIG. 10C and FIG. 10D). The small circle area 1206 is enlarged in FIG. 12D. The two bright spot features 1202 outline groups of pixels identified as potential cancer features. The intensity values for the group of feature pixels in the original image 800 are averaged to yield a feature signal average of 31.6 units based on the scale in the original input image. Similarly, FIG. 12A and FIG. 12C show the same region for the two bright spot features 1202 as in FIG. 12B and FIG. 12D, except with the pixels for the two bright spot features removed. The small circle area 1207 in FIG. 12C and FIG. 12D define a surrounding region centered on the selected two features 1203. The radius of the surrounding region circles 1207 and 1206 is chosen based on historical data calibrated from a control group of samples in order to optimize identification accuracy. The pixels in the small circle 1207 of the surrounding region in FIG. 12C outline groups of pixels identified as background in the original image. The intensity values for the background group of pixels in the original input image 800 are averaged to yield a background signal average of 17.3 units. The ratio between the feature signal average and the background signal average, or a local contrast value is thus 31.6/17.3=1.83, above a preset local contrast threshold of 1.8 set based on historical calibrations. Therefore pixels outlined by the two bright features 1202 in FIG. 12D have signals above the local contrast criteria and satisfy both the size and intensity filtering criteria and are identified as cancer cells.

FIG. 13A and FIG. 13B show a modified input image 1300 and an enlarged area 1320 of the input image, respectively, containing the two cancer cell features 1302 identified by the method as described above using image analysis. FIG. 13B is an image 1320 showing a stained pathology image of the same region of the tissues as pictured by the circled area 1306 in FIG. 13A. The two semi-circular spots 1302 in FIG. 13B are cancer cells according to pathology results and confirms the accuracy of the imaging analysis technique described above in identifying the two cancer spot features 1302.

Depending on the nature of the computing device, one or more additional elements may be present. For example, a smart phone or other portable electronic device may include a camera, capable of capturing still or video images. In some embodiments, a computing device may include sensors such as a global positioning system (GPS) to sense location and inertial sensors such as a compass, an inclinometer and/or ran accelerometer. The operating system may include utilities to control these devices to capture data from them and make the data available to applications executing on the computing device.

As another example, in some embodiments, a computing device may include a network interface to implement a personal area network. Such an interface may operate in accordance with any suitable technology, including a Bluetooth, Zigbee or an 802.11 ad hoc mode, for example.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present application are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present application can be implemented in any of numerous ways. For example, the disclosed method may be applied to imaging methodologies beyond simple fluorescence, including MRI, Ultrasound, Mammography and other X-ray techniques, Raman, Two-Photon Microscopy and others.

For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format. In the embodiment illustrated, the input/output devices are illustrated as physically separate from the computing device. In some embodiments, however, the input and/or output devices may be physically integrated into the same unit as the processor or other elements of the computing device. For example, a keyboard might be implemented as a soft keyboard on a touch screen. Alternatively, the input/output devices may be entirely disconnected from the computing device, and functionally integrated through a wireless connection.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present application as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "code", "program" or "software" are used herein in a generic sense to refer to any type of computer code or set of computer-executable instructions that can be employed to program a computer or other processor to implement various aspects of the present application as discussed above. Additionally, it should be appreciated that according to one aspect of this embodiment, one or more computer programs that when executed perform methods of the present application need not reside on a single computer or processor, but may be distributed in a modular fashion amongst a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present application may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method for detecting cancer cells in situ, comprising acts of:
   collecting a surgical site image;
   indicating, on a display, one or more locations of the detected cancer cells, wherein the detected cancer cells are residual cancer cells remaining after an initial surgery, wherein indicating the one or more locations of the detected cancer cells comprises acts of:
      selecting a portion of the surgical site image responsive to an intensity parameter;
      modifying the selected portion of the surgical site image to identify one or more groups of potential residual cancer cells based on size, wherein each group of potential residual cancer cells comprises a plurality of cells, and wherein the act of modifying comprises filtering the portion of the surgical site image based on a first size threshold;
      analyzing a first group of the one or more groups of potential residual cancer cells by applying a local-based threshold if a size of the first group is below the first size threshold and above a second size threshold that is less than the first size threshold and greater than zero;
      identifying the first group as residual detected cancer cells if the analyzing satisfies a criterion of the local-based threshold; and
      displaying the first group as residual detected cancer cells on the display.

2. The method according to claim 1, further comprising acts of enhancing the surgical site image using one or more methods selected from the group consisting of a difference of Canny Filtering, Sobel Filtering, Kayyali filtering, Principle Curvature-Based region detection, features from accelerated segment testing, Forstner filtering, a Laplacian of Gaussians, Tophat filtering, maximally stable extremum regions, and a determinant of Hessian.

3. The method according to claim 1, wherein the intensity parameter includes an intensity threshold, and wherein the act of selecting comprises selecting the portion of the surgical site image with an intensity higher than the intensity threshold.

4. The method according to claim 3, wherein the act of identifying comprises identifying detected cancer cell regions in the modified selected portion of the surgical site image based on a local contrast threshold.

5. The method according to claim 3, wherein the intensity threshold is calculated based on a statistical average intensity from all pixels in the surgical site image.

6. The method according to claim 5, further comprising an act of receiving the intensity threshold via a manual input by an operator to an image analysis system.

7. The method according to claim 4, wherein the act of identifying the detected cancer cell regions in the modified selected portion of the surgical site image further comprises:
   for each one of one or more continuous pixels in the modified portion of the surgical site image, calculating a first signal mean of the continuous pixels;
   calculating a second signal mean of a surrounding region for each one of one or more of the continuous pixels, wherein the surrounding region is defined by a geometric shape of a predetermined size centered around a center of mass for each one of one or more of the continuous pixels and excluding the continuous pixels;
   calculating a local contrast value by dividing the first signal mean by the second signal mean; and
   identifying the continuous pixels with local contrast values greater than the local contrast threshold as the detected cancer cell regions.

8. The method according to claim 1, wherein the act of displaying comprises highlighting the one or more locations of the identified residual detected cancer cells as a displayed region on the display.

9. The method according to claim 8, wherein the act of highlighting includes using pseudo-coloring and/or at least one type of geometric feature to identify the displayed region on the display.

10. The method according to claim 1, wherein indicating the one or more locations of the detected cancer cells on the display is performed in real time during an operative procedure to remove the detected cancer cells.

11. The method according to claim 1, wherein the act of filtering the portion of the surgical site image based on the first size threshold comprises an act of discarding one or more continuous pixels in the portion of the surgical site image with sizes greater than the first size threshold.

12. The method according to claim 1, wherein the act of filtering the portion of the surgical site image based on the first size threshold comprises an act of filtering with the first size threshold having a value between 100 μm and 1 mm inclusively.

13. The method according to claim 1, wherein collecting the surgical site image comprises collecting the surgical site image from a surgical bed using a photosensitive detector of a handheld medical imaging device.

14. The method according to claim 1, wherein the surgical site image is a fluorescent image.

* * * * *